US011497430B2

(12) United States Patent
Sirendi et al.

(10) Patent No.: US 11,497,430 B2
(45) Date of Patent: Nov. 15, 2022

(54) ANALYSIS OF CARDIAC DATA

(71) Applicant: Transformative AI LTD, Cambridge (GB)

(72) Inventors: Marek Sirendi, Tallinn (EE); Joshua Steven Oppenheimer, Arlington, VA (US); Marek Rei, Cambridge (GB)

(73) Assignee: Transformative AI LTD, Cambridge (GB)

( * ) Notice: Subject to any disclaimer, the term of this patent is extended or adjusted under 35 U.S.C. 154(b) by 92 days.

(21) Appl. No.: 16/491,164

(22) PCT Filed: Mar. 7, 2018

(86) PCT No.: PCT/GB2018/050580
§ 371 (c)(1),
(2) Date: Sep. 5, 2019

(87) PCT Pub. No.: WO2018/162901
PCT Pub. Date: Sep. 13, 2018

(65) Prior Publication Data
US 2020/0008696 A1    Jan. 9, 2020

(30) Foreign Application Priority Data
Mar. 7, 2017  (GB) ..................... 1703662

(51) Int. Cl.
*A61B 5/316*  (2021.01)
*A61B 5/024*  (2006.01)
(Continued)

(52) U.S. Cl.
CPC .......... *A61B 5/316* (2021.01); *A61B 5/02405* (2013.01); *A61B 5/7267* (2013.01);
(Continued)

(58) Field of Classification Search
CPC ... A61B 5/316; A61B 5/02405; A61B 5/7267; A61B 5/7275; A61B 5/024; A61B 5/7282; A61B 5/746
See application file for complete search history.

(56) References Cited

U.S. PATENT DOCUMENTS

| 2002/0068875 A1 | 6/2002 | Schroeppel et al. |
| 2004/0215090 A1 | 10/2004 | Erkkila et al. |

(Continued)

FOREIGN PATENT DOCUMENTS

| EP | 1408829 | 4/2004 |
| EP | 1789907 | 5/2007 |

(Continued)

OTHER PUBLICATIONS

Invitation to Pay Additional Fees, Communication Relating to the Results of the Partial International Search and the Provisional Opinion dated Nov. 8, 2019 From the International Searching Authority Re. Application No. PCT/GB2018/050580. (21 Pages).

(Continued)

*Primary Examiner* — Carl H Layno
*Assistant Examiner* — Aya Ziad Bakkar

(57) ABSTRACT

The present invention relates to a method of analysing cardiac data relating to a patient, comprising: providing cardiac data relating to the patient—optionally by using a means for providing physiological data (20); determining one or more properties of the data, wherein the or each property is determined over a particular context length, the context length being selected based on the or each property—optionally using an analysis module (24); comparing the or each property against a respective predetermined threshold value, thereby to indicate a probability of the patient experiencing a cardiac event—optionally using a means for providing an output (26); and providing an output (Continued)

based on the comparison. A system and apparatus corresponding to this method is also disclosed.

20 Claims, 9 Drawing Sheets

(51) Int. Cl.
 *A61B 5/00* (2006.01)
 *G16H 50/20* (2018.01)
(52) U.S. Cl.
 CPC .......... *A61B 5/7275* (2013.01); *A61B 5/7282* (2013.01); *A61B 5/746* (2013.01); *G16H 50/20* (2018.01)

(56) References Cited

U.S. PATENT DOCUMENTS

| | | | |
|---|---|---|---|
| 2005/0004486 A1* | 1/2005 | Glass ................... | A61B 5/361 600/515 |
| 2005/0137482 A1 | 6/2005 | Laitio et al. | |
| 2009/0259266 A1 | 10/2009 | Zhang et al. | |
| 2011/0028856 A1 | 2/2011 | Zhang | |
| 2012/0179382 A1 | 7/2012 | Zhang | |
| 2012/0310050 A1* | 12/2012 | Osorio ............... | A61B 5/02055 600/300 |
| 2013/0011039 A1 | 1/2013 | Kadir et al. | |
| 2013/0137945 A1 | 5/2013 | Addison et al. | |
| 2014/0257122 A1 | 9/2014 | Ong et al. | |
| 2015/0332012 A1 | 11/2015 | Edelson et al. | |
| 2016/0022162 A1* | 1/2016 | Ong ..................... | A61B 5/7275 600/301 |
| 2016/0106378 A1 | 4/2016 | Kyal et al. | |
| 2016/0135706 A1* | 5/2016 | Sullivan ............... | A61N 1/0484 600/301 |
| 2017/0196769 A1 | 7/2017 | Freeman et al. | |

FOREIGN PATENT DOCUMENTS

| | | |
|---|---|---|
| EP | 3120753 | 1/2017 |
| GB | 2560339 | 9/2018 |
| WO | WO 02/067776 | 9/2002 |
| WO | WO 2014/071145 | 5/2014 |
| WO | WO 2014/147028 | 9/2014 |
| WO | WO 2016/162838 | 10/2016 |
| WO | WO 2016/183683 | 11/2016 |
| WO | WO 2018/162901 | 9/2018 |

OTHER PUBLICATIONS

Invitation to Pay Additional Fees, Communication Relating to the Results of the Partial International Search and the Provisional Opinion dated Oct. 21, 2019 From the International Searching Authority Re. Application No. PCT/GB2019/052223. (14 Pages).
Joo et al. "Prediction of Spontaneous Ventricular Tachyarrhythmia by An Artificial Neural Network Using Parameters Gleaned From Short-Term Heart Rate Variability", Expert Systems With Applications, XP028333859, 39(3): 3862-3866, Feb. 15, 2012.
Lee et al. "Prediction of Ventricular Tachycardia One Hour Before Occurence Using Artificial Neural Networks", Scientific Reports, XP055636082, 6(1): 32390-1-32390-7, Published Online Aug. 26, 2016.
Martinez-Alanis et al. "Quantitative Analysis of Ventricular Ectopic Beats in Short-Term RR Interval Recordings to Predict Imminent Ventricular Tachyarrhythmia", International Journal of Cardiology, XP029794599, 225: 226-233, Available Online Oct. 3, 2016.
Murukesan et al. "Machine Learning Approach for Sudden Cardiac Arrest Prediction Based on Optimal Heart Rate Variability Features", Journal of Medical Imaging and Health Informatics, XP055636086, 4(4): 521-532, Aug. 2014.
Patents Act 1977: Search Report Under Section 17(5) dated Mar. 1, 2019 From the Intellectual Property Office of the United Kingdom of Great Britain Re. Application No. GB1814620.9. (6 Pages).
Patents Act 1977: Search Report Under Section 17(6) and Examination Report Under Section 18(3) dated Dec. 8, 2017 From the Intellectual Property Office of the United Kingdom of Great Britain Re. Application No. GB1703662.5. (8 Pages).
Osowski et al. "Support Vector Machine-Based Expert System for Reliable Heartbeat Recognition", IEEE Transaction on Biomedical Engineering, 51(4): 582-589, Apr. 2004.

\* cited by examiner

ANALYSIS OF CARDIAC DATA

RELATED APPLICATIONS

This application is a National Phase of PCT Patent Application No. PCT/GB2018/050580 having International filing date of Mar. 7, 2018, which claims the benefit of priority of United Kingdom Patent Application No. 1703662.5 filed on Mar. 7, 2017. The contents of the above applications are all incorporated by reference as if fully set forth herein in their entirety.

FIELD AND BACKGROUND OF THE INVENTION

The present invention relates to the analysis of cardiac data, in particular, the invention relates to a system and method of determining the probability of a cardiac event occurring. This may enable timely preventative action to be taken, or may enable the determination of periods where increased monitoring of a person may be beneficial.

There are numerous conditions which may result in the deterioration of a patient's health; accurate prediction of these conditions would, usefully, enable preventative action to be taken. One such condition is sudden cardiac death (SCD), which is death caused by a loss of heart function; this is expressed by sudden loss of consciousness, occurring within 1 hour after the primary onset of the acute symptoms. Despite the harm caused by SCD, there remains difficulty in determining, with a sufficient prediction time, the likelihood of SCD occurring.

Current prediction methods use echocardiography and magnet resonance tomography; whilst these methods can be used to predict long-term risk of cardiac events (over a timescale of months to years), they are, problematically, not currently useable to determine short to medium term risk (minutes to hours/days). It is often not possible, or economical, to monitor a high-risk patient constantly for years, therefore there is needed a method that can indicate the risk of a cardiac event over these shorter timescales.

At present, many patients are continuously monitored in hospital wards and other settings, where measurements of the electrical activity of the heart, such as electrocardiograms, are taken on a regular basis, sometimes continuously. These measurements enable characteristics of cardiac activity to be extracted. However, only minimal processing is applied to the data, resulting in healthcare providers being confronted with large amounts of noisy raw data. While current technology allows for algorithmic analysis and description of the patient's cardiac activity at the time of analysis (and, as aforementioned, potentially allows for determination of a long-term risk), it does not provide predictive analysis of short to medium term potential future cardiac activity. The present invention aims to make the measured data more useful and actionable through sophisticated data analysis and the use of artificial intelligence, so that cardiac events (and more generally periods of increased risk, where additional attention should be given to a patient) may be predicted.

SUMMARY OF THE INVENTION

Aspects and embodiments of the present invention are set out in the appended claims. These and other aspects and embodiments of the invention are also described.

Described herein is a method of predicting cardiac events using heart rate data relating to a patient, comprising [the steps of]: evaluating a property of multiple heartbeats within said heart rate data; determining a value associated with the number of said multiple heartbeats that exceed an abnormality threshold set for said property; and comparing said value against a predetermined value [for a given time window], thereby to indicate a probability of said patient experiencing a cardiac event; wherein the abnormality threshold is determined based on a dataset of a plurality of heart rate data obtained from multiple sources.

Also described herein is a method of predicting cardiac events using physiological data relating to a patient, comprising: inputting physiological data relating to the patient; evaluating a property of multiple heartbeats within the physiological data; determining a value associated with the number of the multiple heartbeats that exceed an abnormality threshold set for said property; comparing the value against a predetermined value, thereby to indicate a probability of the patient experiencing a cardiac event; and providing an output based on the comparison; wherein the abnormality threshold is determined based on a dataset of a plurality of physiological data obtained from multiple sources.

Providing a method of predicting events that are likely to lead to medical conditions enables timely preventative action to be taken. In particular, the method described herein may be used to predict the onset of arrhythmias that are likely to lead to cardiac events (e.g. Sudden Cardiac Arrest). As described herein, this may be achieved by using physiological data to produce a single probabilistic assessment of the likelihood of a patient experiencing a cardiac event in a subsequent time period. The applicable time scales are considered to be from seconds to hours in advance of the episode.

The present invention may help to reduce the workload for healthcare providers by reducing the volume of data they are confronted with. It may also improve outcomes for patients and lead to fewer complications.

According to at least one aspect of the present invention, there is disclosed herein a method of analysing cardiac data relating to a patient, comprising: providing cardiac data relating to the patient; determining one or more properties of the data, wherein each property is determined over a particular context length, the context length being selected based on the property; comparing the or each property against a respective predetermined threshold value, thereby to indicate a probability of the patient experiencing a cardiac event; and providing an output based on the comparison.

A patient, as specified here, may refer to a patient who is currently receiving medical care, for example in a hospital, but could equally relate to, for example, a person not currently receiving care, where cardiac data is obtainable (for example a person with a defibrillator, who is considered healthy).

The threshold value is preferably determined based on a plurality of data obtained from multiple sources, where the plurality of data may come from patient data from a plurality of previous patients.

The method of analysing cardiac data may be used for, and/or described as, a method of monitoring patients, possibly wherein the method of monitoring patients also comprises a method of indicating a period of increased risk. As aforementioned, patient is intended here to cover a broad range of possible users, so that the method may be used for monitoring a user with a wearable heartbeat monitoring device, even if they are not under observation for any medical conditions (and are considered to be healthy). The method could then, in more general terms, be considered a way of monitoring the health of a user.

Each property has a respective context length. The context length may range between 10 and 100,000 heartbeats, approximately. As will be appreciated, 100,000 beats is roughly the average number of heartbeats a human has in a day, though larger context lengths are possible. More preferably, a context length of around 3,600 beats (i.e. roughly an hour), may be considered. More preferably, a context length of around 350 beats (i.e. roughly 5-6 minutes) may be considered. For example, a context length of around 230 beats has been found to yield good results. Preferably, an optimally discriminating context length is determined, where this determination may be performed using a chi-squared ($\chi^2$) test, a Kolmogorov-Smirnov test, and/or an Energy Test. This context length may be the same for the all properties, more preferably each property has a respective context length (determined specifically for that property)

Additional data may be used, where this data is treated similarly to the cardiac data. The method then optionally further comprises: providing further data relating to the patient, wherein the further data comprises at least one of: physiological data, demographic data, admission data, past medical history, laboratory data, imaging data; determining one or more properties of the further data, wherein each property is determined over a particular context length, the context length being selected based on the property; comparing the or each property of the further data against a predetermined threshold value for the further data, thereby to indicate a probability of the patient experiencing a cardiac event; and providing an output based on the comparison. Preferably this output based on the comparison of the further data is combined with the comparison of the (cardiac) data to obtain a combined output.

The data preferably comprises data from multiple heartbeats, more preferably RR intervals of multiple heartbeats, where these are, for example, indicated on an electrocardiogram (ECG). In order to reduce the processing load, the data may be processed in batches, preferably of at least 5 heartbeats, more preferably of between 5 and 15 heartbeats, yet more preferably of 10 heartbeats. This enables more accurate algorithms to be used with the (batched) data.

The properties are preferably properties of multiple heartbeats, such as a mean, a standard deviation, or a standard deviation in successive differences (related to the multiple heartbeats). Optionally, the properties also comprise a measured heart rate variability (HRV), which may be obtained from the RR intervals, and/or a fraction of multiple heartbeats which exceed an abnormality threshold (this may be, for example the fraction of RR intervals related to each heartbeat which exceed an interval).

According to another aspect of the present invention, there is disclosed a method of analysing cardiac data relating to a patient, comprising: providing cardiac data relating to the patient; determining one or more properties of the data; comparing the or each property against a respective predetermined threshold value, thereby to indicate a probability of the patient experiencing a cardiac event; and wherein the property comprises a fraction of the multiple heartbeats that exceed an abnormality threshold; and providing an output based on the comparison.

A rate of change of the or each property is optionally determined, where this may be used to determine an urgency, or may be used to give a further output. This may be separate to any other outputs, or may be combined with other outputs. The method preferably uses a plurality of properties within the data to provide a more accurate output.

If the probability of a cardiac event occurring in a subsequent time period exceeds a certain threshold, a warning may be issued and the healthcare provider notified. This should enable appropriate action to be taken to prepare for an appropriate response to the cardiac event and/or prevent the arrhythmia from occurring, such as by administering medications or running diagnostic tests. Thus, the predetermined value is determined optimally to separate normal and arrhythmic patients.

The probability of a cardiac event is preferably determined using Bayesian inference, where this is used to reduce the number of false positives, or false negatives by creating a link between the predicted (indicated) probability and a prior distribution.

According to yet another aspect of the current invention, there is disclosed a method of analysing data relating to a patient, comprising: providing cardiac data relating to the patient; determining one or more properties of the data; comparing the or each property against a respective predetermined threshold value, thereby to indicate a probability of the patient experiencing a cardiac event; wherein the indicated probability is calculated using Bayesian inference; and providing an output based on the comparison.

There is preferably also presented a measure of the uncertainty related to the indicated probability, where this preferably includes displaying at least one of: a standard deviation, and error bounds. This allows a user to better assess the data as compared to a probability in isolation.

The probability is optionally characterised with a measure of the skew of the probability distribution, such as a kurtosis. The probability may be presented as a probability density function (or a cumulative probability function), where this may be displayed graphically, or numerically.

This probability is preferably updated periodically, where the time intervals for the updates may depend on the situation. Where the processing volume is not a major consideration, the time intervals may be small enough to be effectively continuous (e.g. they may be less than a second). Where computing power is more of a concern, the time intervals may be at least 5 seconds, or between 10 seconds and 30 seconds, where these values may reduce the computational burden while keeping the risk of missing a cardiac event very low. Where computing power is a major concern, such as in implanted devices, which have a limited battery, the time intervals may be at least 5 minutes, or at least an hour.

Preferably, the time intervals are dependent upon the currently indicated probability, where a very low probability may enable longer time intervals to be used while maintaining a low risk of missing a cardiac event. If this probability begins to increase, the time intervals may be shortened. To further reduce the risk of missing an event, there is preferably a maximum time interval.

The probability preferably comprises an indication of a corresponding time, where this may be an amount of time (i.e. a probability is of an event within x minutes) or one or more time windows (e.g. a probability $P_1$ of an event between x and y minutes, and a probability $P_2$ of an event between y and z minutes). A probability may also display one or more period(s), or time(s), of highest risk, or heightened risk, where this may be related to a probability exceeding a threshold probability of a cardiac event. This may be used to indicate a period over which a user should be monitored more carefully.

The threshold value against which the property is compared is preferably determined using at least one of: a long short-term memory unit, adversarial training, multi-task training, an attention mechanism, and a computationally minimalistic algorithm. These techniques may, for example, increase accuracy and/or reduce computational burden.

The method optionally also uses an Energy Test to analyse the cardiac data, where the method further comprises: determining an Energy Test metric by performing an Energy test on at least one of the one or more properties of the data; comparing the Energy Test metric to a predetermined threshold value; and presenting an output when the Energy test metric exceeds a predetermined threshold.

According to yet another aspect of the present invention, there is disclosed a method of analysing cardiac data relating to a patient, comprising: providing cardiac data relating to the patient; determining one or more properties of the data; determining an Energy Test metric by performing an Energy test on at least one of the one or more properties of the data; comparing the Energy Test metric to a predetermined threshold value; and presenting an output when the Energy test metric exceeds a predetermined threshold.

As has been previously demonstrated in published research, computing features based on RR interval sequences and training classifiers based on these features enables a probabilistic assessment to be made. However, as measurements of individual heartbeats are susceptible to noise and instrumental fault, a more robust decision-making mechanism is herein provided for deciding whether to issue alerts of a possible oncoming cardiac event.

Optionally, the evaluated property is a property of cardiac data. Preferably, the evaluated property is the RR intervals of multiple heartbeats, for example as indicated on an electrocardiogram (ECG). Optionally, said value is compared against a predetermined value for a given time window. Optionally, said value is the fraction of said multiple heartbeats that exceed the abnormal threshold (e.g. the number of heartbeats exceeding the abnormal threshold as a fraction of the total number of heartbeats being evaluated).

The method may determine the abnormality threshold by training at least two classifiers (which may optionally be cardiac classifiers) to classify a property of multiple heartbeats within the physiological data using at least one machine learning algorithm; and combining the at least two classifiers to produce a hybrid classifier; wherein the combination is based on a performance metric.

According to yet another aspect of the present invention, there is disclosed a method of training a hybrid classifier for prediction of cardiac events based on physiological (preferably cardiac) data, the method comprising the steps of: training at least two classifiers to classify a property of multiple heartbeats within the physiological data using two or more different machine learning algorithms; and combining the at least two classifiers to produce a hybrid classifier; wherein the combination is based on a performance metric.

As described herein: the abnormality threshold may be determined by: training at least two (preferably cardiac) classifiers to classify a property of multiple heartbeats within said physiological data using at least one machine learning algorithm; and combining said at least two classifiers to produce a hybrid classifier; wherein said combination is based on a metric.

The metric is preferably a performance metric.

Preferably, at least two different machine learning algorithms are preferably used to obtain a result which is less susceptible to flaws within a machine learning algorithm (as different algorithms may be give erroneous results in different situations).

Also described herein is a method of training a hybrid classifier for prediction of cardiac events based on physiological data, the method comprising the steps of: training at least two (preferably cardiac) classifiers to classify a property of multiple heartbeats within said physiological data using one or more machine learning algorithms; and combining at least two classifiers to produce a hybrid classifier; wherein said combination is based on a metric.

As mentioned above, the evaluated property may be a property of cardiac data, and preferably the RR intervals of multiple heartbeats. The at least two (i.e. two or more) classifiers may be trained simultaneously. The metric may comprise at least one of: an accuracy; a sensitivity; and a specificity. The one or more machine learning algorithms may comprise at least one of: an Artificial Neural Network; a Support Vector Machines; a k-Nearest Neighbours algorithm; a Gaussian process; and a Random Forest. All of said classifiers may be trained and combined (and/or added together).

One of the algorithms used optionally comprise a neural network, preferably a convolutional neural network.

A distilling method is preferably used within the training of the classifiers, where this comprises: training a first neural network; and training a second neural network dependent upon the output of the first neural network. Distilling, as described, may be used to train a second, simpler and faster, model from a first model.

When using a Gaussian process, preferably a limited number of datapoints are used, preferably where this limited number is no more than 3,000. This has been found to result in an improved classifier.

The hybrid classifier may be further configured to output a weighted sum of the outputs of the at least two classifiers. The weights in the weighted sum may be determined from a measure of performance of each of the classifiers in the hybrid classier.

The root mean square error (RMSE) may be used to determine an optimal combination of classifiers. This RMSE is preferably the RMSE over misclassifications.

As aforementioned, testing time domain measures for optimal context may be determined by performing a chi-squared ($\chi^2$) test of compatibility on different context lengths. Context lengths from 10 to 100,000 beats may be considered during the chi-square ($\chi^2$) test. As mentioned above, preferably a context length of under an hour, or around 3,600 beats, may be considered. More preferably, a context length of around 350 beats may be considered. For example, a context length of around 230 beats has been found to yield good results.

Maximally discriminating lengths may be determined for each feature individually prior to training the classifiers, thereby to achieve enhanced separation power.

There are multiple ways to measure the performance of a classification task. Commonly used metrics include accuracy, sensitivity, specificity, F-score, and precision. However, optimising the hyper-parameters of an algorithm based on any one of these metrics leads to suboptimal performance overall. In the method described herein, a custom proper score is employed to achieve maximally discriminating results. Specifically, the RMSE evaluated for misclassifications is minimised at multiple stages of the method including at the neural network training, heartbeat-level and patient-level separation steps.

In the method described herein, multiple heartbeats, each with corresponding contexts, may be evaluated before a decision to issue an alert is made. The fraction of heartbeats that exceed an abnormality threshold is computed. Alerts are only issued after the fraction has been evaluated in an appropriate time window and found to exceed a value that optimally separates normal and arrhythmic patient groups.

A hybrid classifier leverages the strength of each method and results in more robust performance. In the method described herein the root mean square error (RMSE) is employed to arrive at an optimal combination of classifiers.

The method described herein tests time domain measures for optimal context. Context lengths from 10 to 100,000 beats (more preferably context lengths from 10 to 3,600), for example, context lengths from 10 to 350 beats, are considered and a chi-square test of compatibility is performed. Maximally discriminating lengths are determined for each feature individually prior to training the classifiers thus achieving enhanced separation power. Previously, a default five-minute window was used in computation of features, based on a qualitative understanding of the heart and commonly used heuristics in the field. Until now, however, no attempt has been made to determine if a five minute window is actually appropriate for all features and/or if optimal discriminating power is achieved for all variables with such a predetermined time window.

Also disclosed herein is a method of monitoring patients using any of the above methods.

Also described herein is a system for predicting cardiac events using physiological data relating to a patient, comprising: means for providing physiological data relating to the patient; and an analysis module configured to evaluate a property of multiple heartbeats in the physiological data, determine whether said property exceeds an abnormality threshold and derive a probability of the patient experiencing a cardiac event; and means for providing an output; wherein the analysis module is configured to trigger an output if the probability of the patient experiencing a cardiac event in the subsequent time period is greater than a predefined threshold.

According to at least one aspect of the present invention, there is also disclosed herein a system for analysing cardiac data relating to a patient, comprising: means for providing cardiac data relating to the patient; an analysis module for determining one or more properties of the data, wherein each property is determined over a particular context length, the context length being selected based on the property; a comparison module for comparing the property against a predetermined threshold value, thereby to indicate a probability of the patient experiencing a cardiac event; and a presentation module for providing an output based on the comparison.

The analysis module may comprise a hybrid classifier trained according to the method described above and herein.

Optionally, the means for providing cardiac data relating to the patient comprises a spatially separated measurement module. This may be used, for example, where a patient is using an implantable device. Data recorded by this device may be provided to a (spatially separate) server, where it is analysed. An output may then be displayed to the user and/or another person (such as a doctor).

According to at least one aspect of the present invention, there is also disclosed herein a client terminal connectable to the system disclosed, where this may be used to access the output in a format desirable to the user. This may, for example, be a handheld portable device which a user could use to connect to a server which performs the methods disclosed herein. Such a server is also disclosed herein.

The physiological (preferably cardiac) data may be provided by/obtained (e.g. sourced) from at least one of: an electrocardiogram (ECG) machine; a pulsometer; a wearable cardioverter defibrillator; an implantable cardioverter defibrillator; a respiratory monitor; and a capnography monitor, or other such source extracting data from the cardiorespiratory system of a patient. The analysis module may comprise a hybrid classifier trained as described above and herein.

According to at least one aspect of the present invention, there is also disclosed herein a portable and/or wearable device, which is configured to carry out the disclosed methods.

Also described herein is a machine learning algorithm for predicting cardiac events. The invention extends to a method and/or a system for predicting a cardiac event substantially as described herein and/or as illustrated in the accompanying figures.

From a physiological standpoint, the method described herein is configured to probe the behaviour of the autonomous nervous system by measuring heart rate variability (HRV) using physiological data. Optionally, respiratory rate variability may be used in addition to cardiac data. Further features may be developed based on respiratory rate variability and included as additional input to the classifiers during training.

A database containing 132 recordings of episodes of Ventricular Tachyarrhythmia (VTA) and 126 control samples was used in the development of the method described herein, i.e. the "Spontaneous Ventricular Tachyarrhythmia (VTA) Database", obtained from Medtronic, Inc. (http://www(dot)physionet(dot)org/physiobank/database/mvtdb/). The subject patient group consisted of implantable cardioverter defibrillator (ICD) users, whereby ICDs are single lead devices developed by Medtronic in this instance. As such the recordings were a mix of at-rest and ambulatory measurements.

In particular, the method described herein was developed using RR intervals (based on the above-mentioned VTA Database) that enable heart rate variability (HRV) analysis to be performed. Other information present on an ECG or extracted from other monitoring devices may be incorporated, however. Respiratory data may also be added as an input.

As used herein, the term "RR interval" preferably refers to an interval from the peak of one "QRS complex" to the peak of the next "QRS complex" (i.e. the time interval between two consecutive "R waves") seen on an electrocardiogram (ECG). The RR interval may be used to assess the ventricular rate. Such data can also be extracted from pulsometers. As used herein, the term "QRS complex" preferably refers to a combination of three graphical deflections seen on an ECG, which is usually the central and most visually obvious part of the tracing on the ECG. It corresponds to the depolarization of the right and left ventricles of the human heart. Both features can be seen on the exemplary ECG illustrated in FIG. 1.

As used herein, the term "cardiac event" preferably connotes a change in the cardiac rhythm of a patient, for example from normal sinus rhythm to an arrhythmia; from one type of arrhythmia to another; or a change in the severity or dangerousness of a cardiac rhythm. In particular, cardiac events may refer to changes which may cause sudden cardiac death (SCD), such as the occurrence of ventricular tachyarrhythmias.

As used herein, except where the context requires otherwise, the term "comprise" and variations of the term, such as "comprising", "comprises" and "comprised", are not intended to exclude further additives, components, integers or steps.

The invention extends to methods, system and apparatus substantially as herein described and/or as illustrated with reference to the accompanying figures.

The invention also provides a computer program or a computer program product for carrying out any of the methods described herein, and/or for embodying any of the apparatus features described herein, and a computer readable medium having stored thereon a program for carrying out any of the methods described herein and/or for embodying any of the apparatus features described herein.

The invention also provides a signal embodying a computer program or a computer program product for carrying out any of the methods described herein, and/or for embodying any of the apparatus features described herein, a method of transmitting such a signal, and a computer product having an operating system which supports a computer program for carrying out the methods described herein and/or for embodying any of the apparatus features described herein.

The invention also provides a computer program and a computer program product comprising software code adapted, when executed on a data processing apparatus, to perform any of the methods described herein, including any or all of their component steps.

The invention also provides a computer readable medium having stored thereon the computer program as aforesaid.

Other aspects of this system, client device and/or method may be implemented in software running on various interconnected servers, and it is to be appreciated that inventive aspects may therefore reside in the software running on such servers.

The invention also extends to a server or a plurality of interconnected servers running software adapted to implement the system or method as herein described.

Any feature in one aspect of the invention may be applied to other aspects of the invention, in any appropriate combination. In particular, method aspects may be applied to apparatus aspects, and vice versa.

Furthermore, features implanted in hardware may generally be implemented in software, and vice versa. Any reference to software and hardware features herein should be construed accordingly.

Any apparatus feature as described herein may also be provided as a method feature, and vice versa. Furthermore, as used herein, means plus function features may be expressed alternatively in terms of their corresponding structure.

It will be appreciated that particular combinations of the various features described and defined in any aspects can be implemented and/or supplied and/or used independently. In other words, any feature in a particular aspect may be provided independently and/or applied to other aspects, in any appropriate combination.

BRIEF DESCRIPTION OF THE SEVERAL VIEWS OF THE DRAWINGS

At least one exemplary embodiment of the present invention will now be described with reference to the accompanying figures, wherein similar reference numerals may be used to refer to similar features, and in which.

DESCRIPTION OF SPECIFIC EMBODIMENTS OF THE INVENTION

In what follows, cardiac data that terminate with a Ventricular Tachyarrhythmia (VTA) is referred to as 'arrhythmic', and cardiac data from control samples is labelled as 'normal'.

Prediction Method for Use on Patients

Figure 2A:
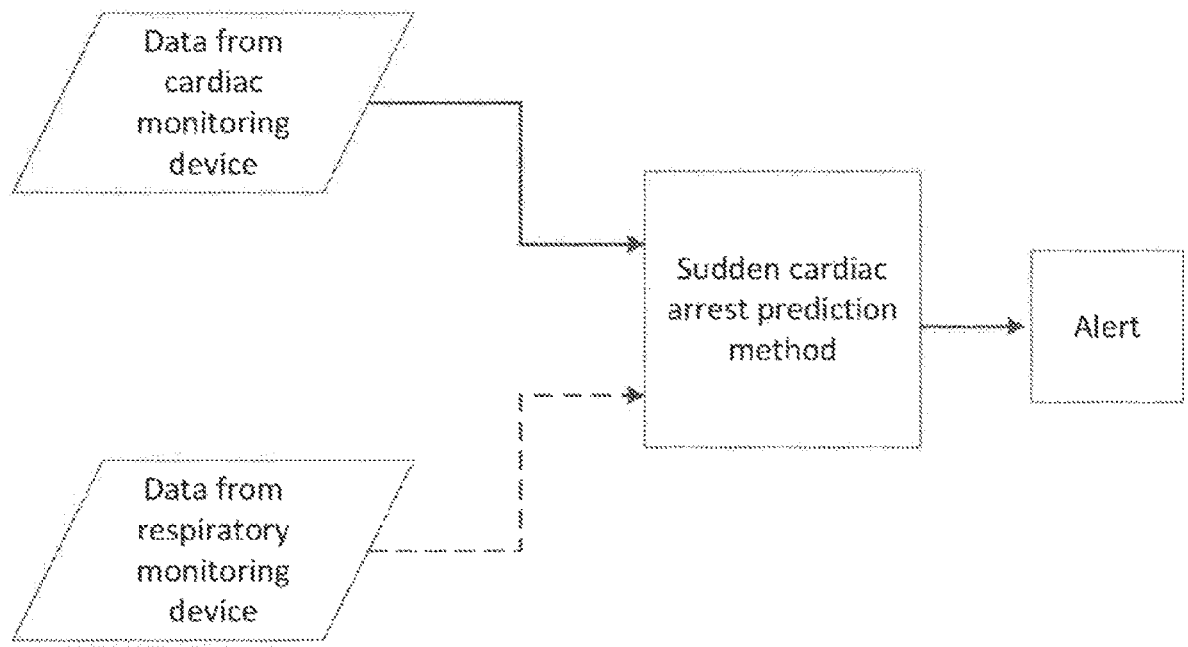
FIG. 2a is a general process flowchart for the method described herein.

FIG. 2a illustrates a method of predicting cardiac events. Physiological data, obtained from a monitoring device are input into an analysis module comprising a pre-trained classifier. The physiological data can comprise data relating to the patient that is collected in real time, for example cardiac data. In some embodiments, the physiological data alternatively or additionally comprises respiratory data relating to the patient collected from a respiratory monitoring device, which are also input into the pre-trained classifier.

The analysis module uses the input physiological data to analyse the heartbeat of the patient, and determine one or more probabilities of the patient experiencing a cardiac event within a period of time in the future.

Figure 1:
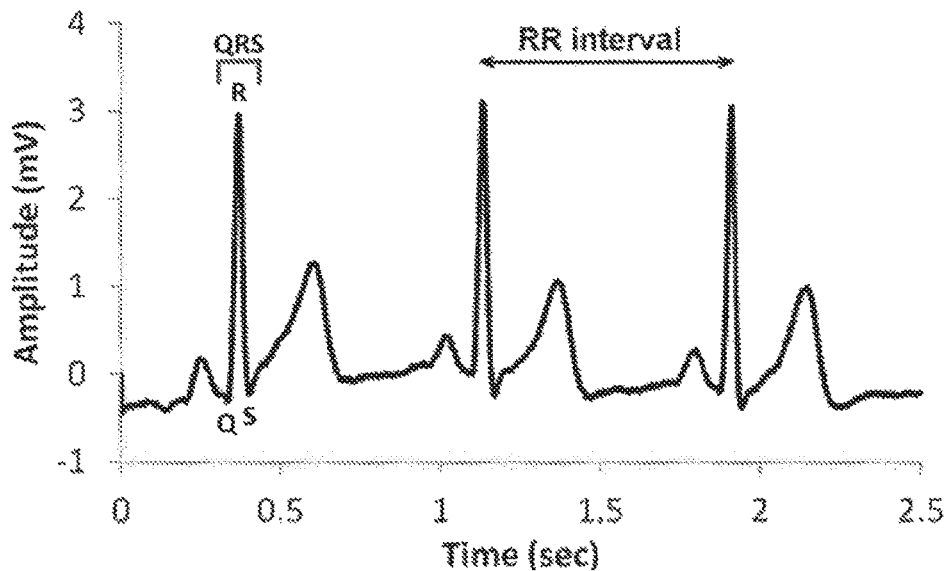
FIG. 1 shows an example of a typical electrocardiographic tracing.

RR interval sequences, as illustrated in FIG. 1, are taken as input, data analysis is performed, and a classifier separates 'arrhythmic' and 'normal' beat sequences. The classifier attributes a probability to each heartbeat and then aggregates the output into an abnormality fraction in [0,1] that forms the basis for a decision to alert the healthcare provider. The abnormality fraction may thereby serve as a useful, actionable, easy-to-interpret number that may guide healthcare providers, patients, or other people who may be in a position to assist the patient. The warning may enable preparation for an appropriate response to the cardiac event and/or prevention of the cardiac event, such as by administering medications and running diagnostic tests.

The method will now be described in more detail, with reference to the process flow illustrated in FIG. 2b. Physiological data, in this example in the form of RR intervals, are input into the analysis module from a monitoring device. Physiological data may contain false measurements (e.g. "outliers") owing, for example, to movement of the patient and/or poor connections in the monitoring device, which lead to artefacts in the datasets.

Patients that suffer from VTAs are also likely to suffer from ectopic beats such as premature ventricular complexes. Therefore, as indicated in the process flow in FIG. 2b, it is necessary to identify and remove any outliers from the physiological data. This may be achieved using, for example, criteria described in G. D. Clifford, F. Azuaje, and P. E. McSharry, *Advanced Methods and Tools for ECG Data Analysis,* Artech House Publishers, 2006. The presence of ectopic beats is, however, recorded and used in the subsequent analysis (see below).

Figure 3A:
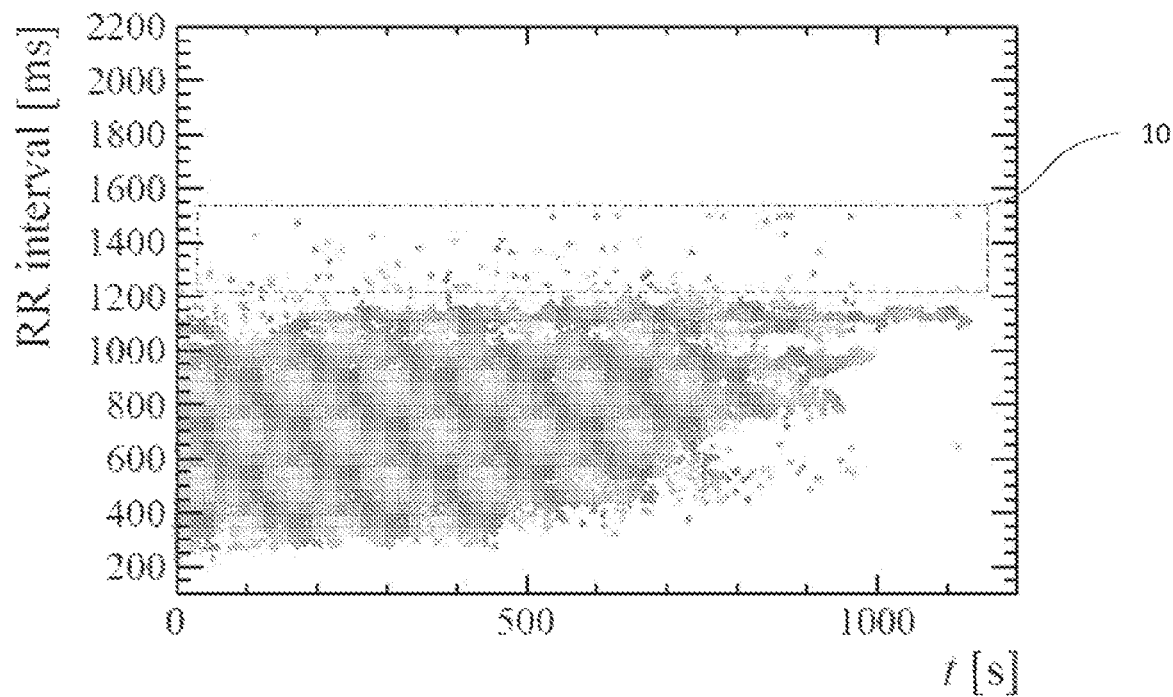
FIGS. 3a and 3b show all of the heartbeats in a "Spontaneous Ventricular Tachyarrhythmia (VTA) Database", before and after outliers have been removed, respectively.
Figure 3B:
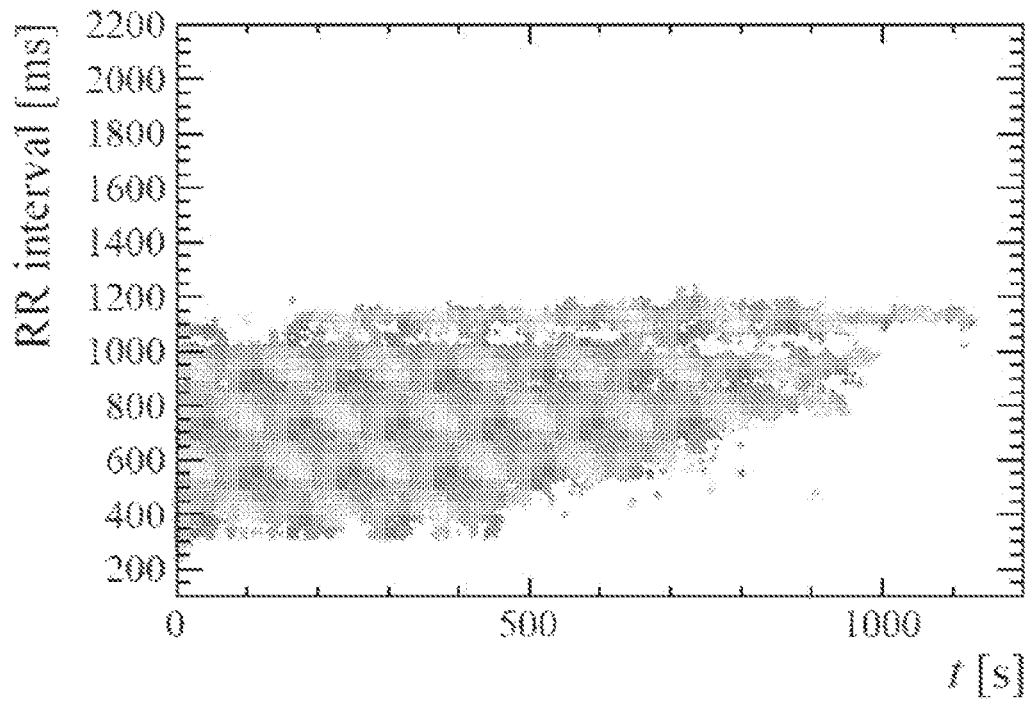

The effect of outlier removal on the data is illustrated in FIGS. 3a and 3b. FIG. 3a illustrates the raw RR interval data taken from the "Spontaneous Ventricular Tachyarrhythmia (VTA) Database", which comprises multiple outlying datapoints 10. The cleaned version of the same data is shown in FIG. 3b.

The cleaned physiological data are then pre-processed as indicated in the process flow of FIG. 2b to obtain unbiased measurements of frequency domain parameters (as discussed below). More specifically, the data first undergoes cubic spline interpolation, and is then resampled at, for example, 7 Hz. Subsequently, the spectral power is computed using a Welch periodogram, for example with a 256-point window overlapped at 50%.

A series of derived quantities are computed based on RR interval data. The derived quantities (listed below) are referred to (interchangeably) as 'features' or 'properties':

i) Time Domain
The arithmetic mean, $\mu$ of the RR intervals;
The standard deviation, $\sigma$ of the RR intervals;
The standard deviation in successive differences, $\sigma_{Diff}$, of the RR intervals.

The distribution of RR intervals in the time domain can provide valuable data relating to the probability of a patient undergoing a cardiac event.

Figure 4:
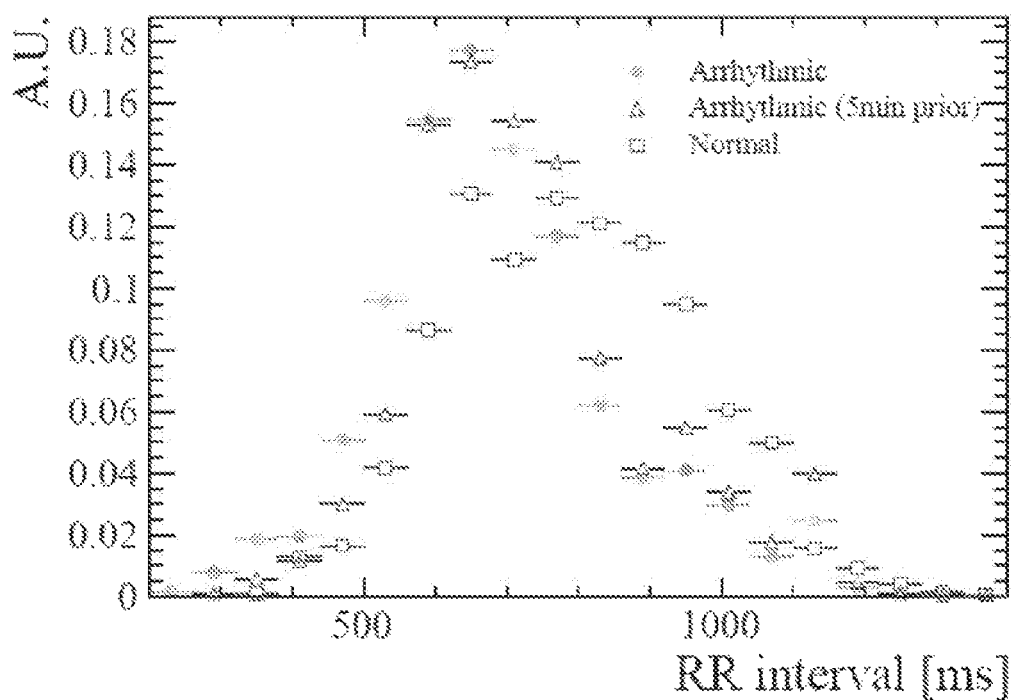
FIG. 4 shows a the distribution of RR intervals for a heart leading up to an arrhythmia (circles), the same distribution with 5 minutes of data removed prior to the episode (triangles) and a normally functioning heart (squares)]

For example, FIG. 4 illustrates distributions of RR intervals for Arrhythmic and Normal sets of heartbeats, measured in arbitrary units (A.U.). The distribution of normal heartbeats is shown using squares, while that of the arrhythmic heartbeats is shown using circles. Furthermore, the distribution of arrhythmic heartbeats with five minutes of data prior to the arrhythmia is shown using triangles.

Figure 5:
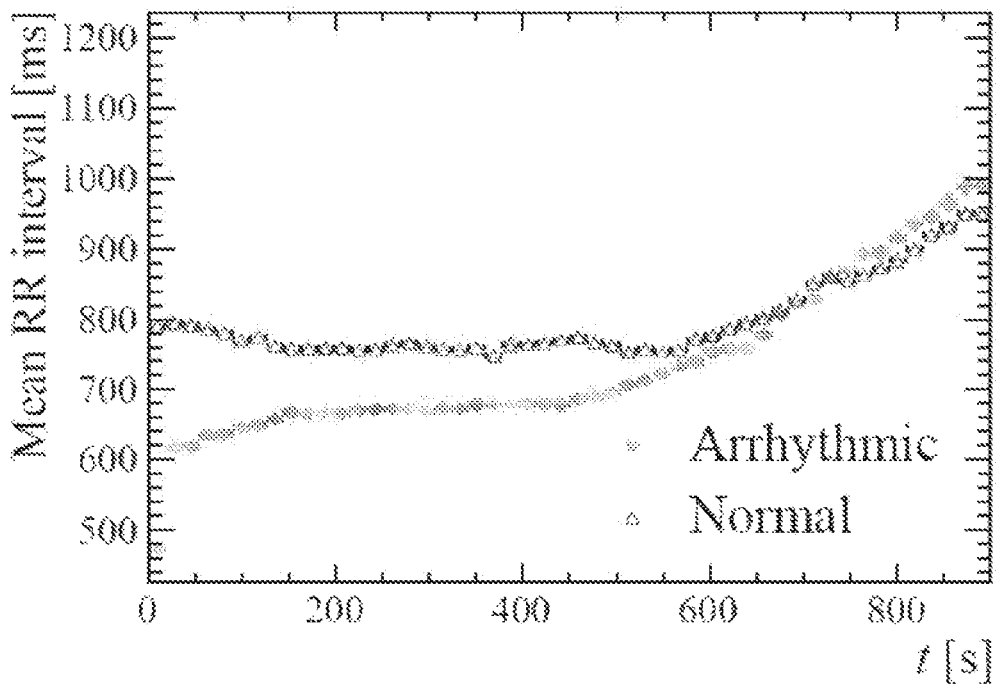
FIG. 5 shows the time evolution of the mean RR interval leading up to an arrhythmia at t=0 s for the 'arrhythmic' distribution.

FIG. 5 shows the time evolution of the mean RR interval leading up to an arrhythmia at t=0 s for the 'Arrhythmic' distribution. In particular, FIG. 5 illustrates the dramatic drop in mean RR intervals at the onset of the arrhythmia near t=0 s.

Figure 6:
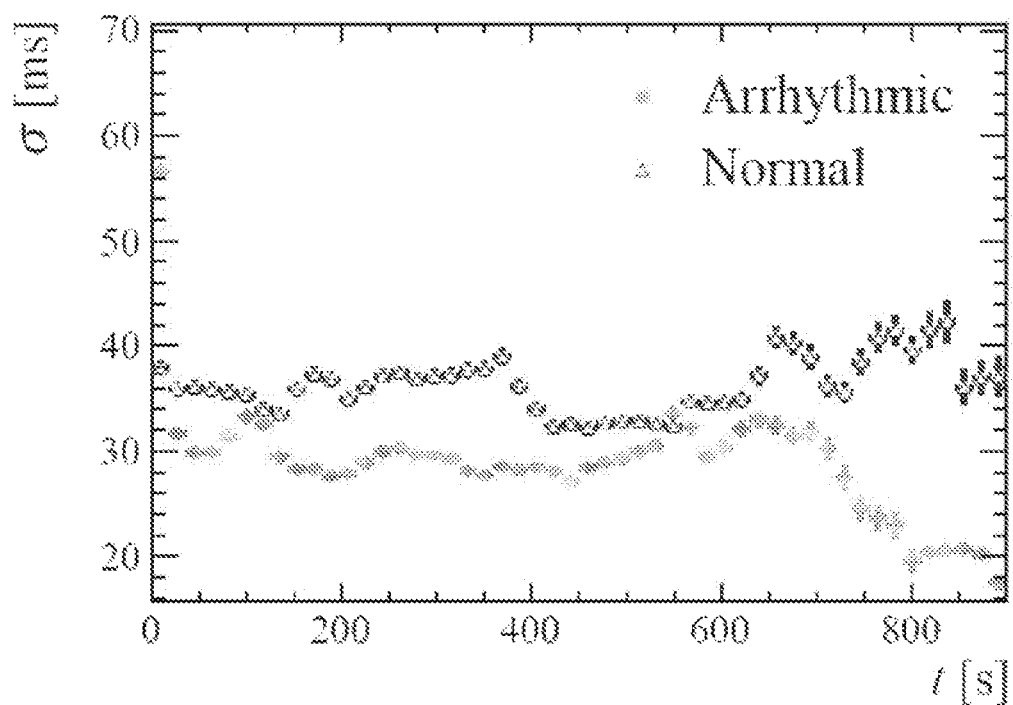
FIG. 6 shows the time evolution of one of the time domain inputs to the algorithm, the standard deviation in RR intervals.

FIG. 6 shows the time evolution of one of the time domain inputs to the algorithm, the standard deviation in RR intervals. The cardiac event occurs at t=0 s, which appears at the leftmost point of the x-axis. Time flows from right (the past) to left (terminating at the event).

ii) Nonlinear Poincaré
Poincaré nonlinear analysis variables, SD1, SD2, and SD1/SD2.

A Poincaré HRV plot is a graph in which successive RR intervals are plotted against one another. From this plot values for SD1 (the dispersion of points perpendicular to the line of identity) and SD2 (the dispersion of points parallel to the line of identity) are determinable. These plots, and the determination of the SD1 and SD2 values, are well known. SD1, SD2, or a combination of SD1 and SD2 are used as inputs to the AI classifier.

iii) Sample Entropy
Sample entropy over four epochs, S1, S2, S3 and S4.

iv) Frequency Domain
Frequency domain parameters, VLF, LF, HF and LF/HF, derived from the spectral power calculated from the Welch periodogram.

v) Ectopic Beat Frequency
The relative frequency of ectopic beats, $f_e$.

The optimal context for each feature, i.e. the optimal—or maximally discriminating—'context length' (as discussed below) for determining whether a feature is indicative of a cardiac event, is determined before each feature is input into an Artificial Intelligence based classifier.

The features derived from the RR interval data are input into an Artificial Intelligence Based Classifier (the AI classifier). The AI classifier can comprise a pre-trained classifier, or preferably multiple pre-trained classifiers combined into a hybrid classifier, that has been trained (as described below) to identify abnormal beats in the physiological data by assigning a probability (i.e. a number in [0,1]) to each heartbeat that reflects the likelihood for the given heartbeat to lead to an arrhythmic episode.

In order to arrive at a robust decision, the number of 'abnormal' heartbeats (e.g. which cross a threshold probability) are counted, and the fraction of said 'abnormal' heartbeats occurring in a given time window (for example, five minutes) is computed. This leads to an abnormality fraction, F, which is attributed to each patient. A 'yes/no' decision is then made based on this fraction, and an alert may be issued (or another action taken) for positive decisions. The alert may, for example, indicates that a cardiac event is predicted; in some embodiments, it also provides additional data related to the probability of the event occurring.

The counting of 'abnormal' heartbeats may also be used to obtain a rate of change of the occurrence of 'abnormal' heartbeats, where this rate of change may be used to identify both that a cardiac event is likely, and also to predict an urgency—where a high rate of change may indicate that a cardiac event is likely to occur soon.

Classifier Training/Architecture

The AI classifier can be trained by a machine learning system receiving as input examples of heartbeats from a training dataset comprising known normal and abnormal heartbeats from which the system can learn to predict whether an arrhythmia is going to occur. Each heartbeat in the training data set is represented as a real-valued vector containing values for features that describe the specific heartbeat, and enable a classification to be made. The training data is pre-processed in the same way as described above in relation to FIG. 2b, providing the same features that will be used in the prediction method for use in the training process.

There is freedom in the number of preceding heartbeats that should be included in the computation of a feature. This is referred to herein as 'context length'. Multiple context lengths from 10 beats to 100,000 beats (though preferably context lengths of less than around 3,600) are considered as variables for time domain measures ($\mu$, $\sigma$, and $\sigma_{Diff}$) and Poincaré nonlinear analysis.

A $X^2$-test ('chi-squared' test) for statistical compatibility is performed for each 'feature' (i.e. derived quantity) and each context length between the 'arrhythmic' and 'normal' data sample distributions. Context lengths that are optimally discriminating, i.e. where the data range is the most significant for detecting a cardiac event, can then be selected as evidenced by a large $X^2$/ndf between the respective distributions, where "ndf" is the number of degrees of freedom.

Figure 7:
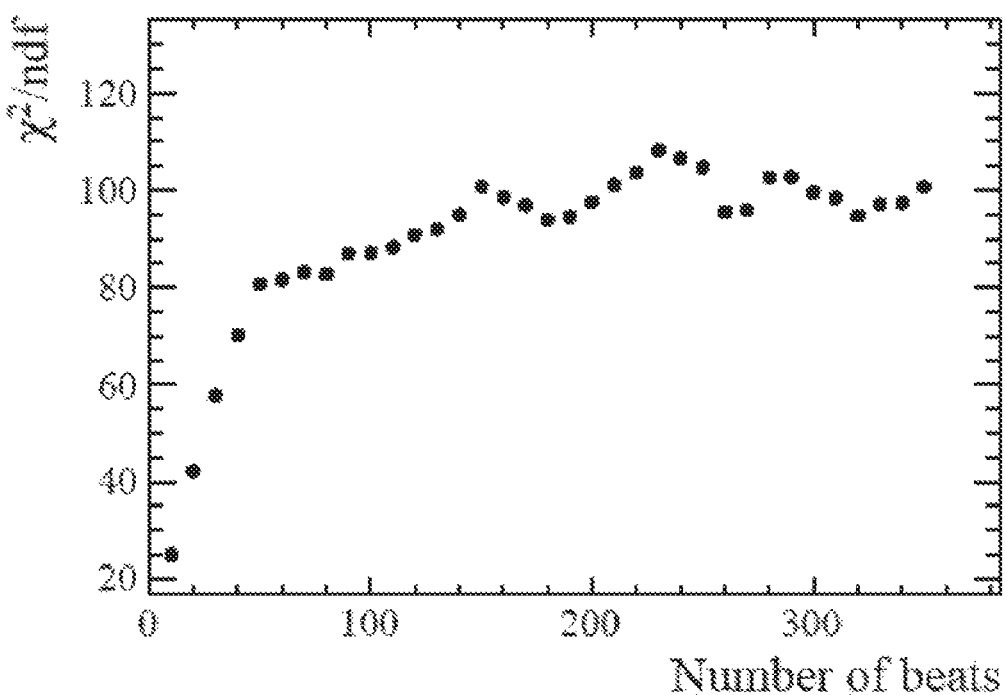
FIG. 7 shows the statistical compatibility of the SD2 variable between the 'arrhythmic' and 'normal' distributions as a function of the number of beats included in the computation.

For example, the $X^2$/ndf for different context lengths for the SD2 variable is shown in FIG. 7 to illustrate that a context length of 230 beats is optimally discriminating for this variable. Determining the optimal context length preferably occurs prior to training. The context length is then held constant during the classifier training phase.

A maximum context length may also be enforced in order to limit the data storage needed, and the recording time needed. The 3,600 beats mentioned previously may be used to limit the amount of data which must be considered.

In order to use the available dataset maximally, a 10-fold cross-validation is performed, whereby the dataset is divided into ten parts and the model is trained ten times. Each time, eight parts are used for training, one part for hyper-parameter tuning and one part for testing. The assignment of different folds is rotated during the ten times.

Five separate machine learning algorithms, in particular, can be used in order to train classifiers (although this method is, of course, extendable to other algorithms). The algorithms are then, preferably, later combined to form a hybrid algorithm, in order to take advantage of each of their strengths.

In some embodiments, the classifier is a long short-term memory unit which may record values over an arbitrary time interval. This type of classifier is particularly useful for processes which have time lags between events (such as cardiac events).

In some embodiments, a convolutional neural network could be used to detect patterns within the recorded data, where this may be combined with an attention mechanism. An attention mechanism enables the neural network to 'learn' where it needs to focus and dynamically assign more importance to those areas. The attention mechanism calculates a weight for each time-window in the input stream and uses it to scale the importance of information coming from that window. This method has been shown to be very successful in other domains such as language processing and also enables visualisation of where the model is focusing, thereby making the actions of the system more human-interpretable.

1. Artificial Neural Network

The feature vectors are given as input to an artificial neural network consisting of three layers. The first layer is an "input layer", the size of which depends on the number of features in the feature vectors. The second layer is a "hidden layer" with tanh activation, with size 10. And finally, the third layer is a single neuron with sigmoid activation. The neurons in the hidden layer will automatically discover useful features from the input data. The model can then make a prediction based on this higher-level representation. The network may be optimised using AdaDelta, for example. Parameters may be updated based on mean squared error as the loss function. The model may be tested on the development set after every full pass through the training data, preferably wherein the best model is used for final evaluation.

2. Support Vector Machines (SVM)

Support Vector Machines (SVM) are a separate class of supervised machine learning algorithms. Instead of focusing on finding useful features, they treat the problem as a task of separation in a high-dimensional space. Given that the feature vectors contain n features, they aim to find an n-1 dimensional hyperplane that best separates the positive and negative cases. This hyperplane is optimised during training so that the distance to the nearest datapoint in either class is maximal.

3. k-Nearest Neighbours k-Nearest Neighbours (k-NN) is an algorithm that analyses individual points in the high-dimensional feature space. Given a new feature vector that we wish to classify, k-NN returns k most similar points from the training data. Since we know the labels of these points, k-NN assigns the most frequent label as the prediction for the new point. This offers an alternative view to the problem—it no longer assumes that heartbeats of a single class are in a similar area in the feature space, but instead allows us to look for individual points that have very similar features.

4. Gaussian Process

Gaussian Process is a statistical model where each datapoint is associated with a normally distributed random variable. The Gaussian Process itself is a distribution over distributions, which is learned during training. This model associates each prediction also with a measure of uncertainty, allowing us to evaluate how confident the model is in its own classification. As this type of model is difficult to train with more than 3,000 datapoints, it is preferable to ensure that a suitable size is sampled during training.

5. Random Forest

Random forests are based on constructing multiple decision trees and averaging the results. Each decision tree is a model that attempts to separate two samples based on sequential splittings for each input feature. In this implementation, datapoints that are misclassified are given a weight larger than one (referred to as 'boosting').

Each classifier assigns a probability (i.e. a number in [0,1]) to each heartbeat that reflects the likelihood for the given heartbeat to lead to an arrhythmic episode. Several different thresholds for the probability may be considered and the value that optimally separates the 'arrhythmic' and 'normal' datasets is chosen. This may be referred to as optimal classification separation.

In some embodiments, the methods of predicting cardiac events are used (and/or embedded) within a portable device, such as a pacemaker, or an implantable cardioverter-defibrillator. Within such a device, it is important that computations are minimised, to maximise the battery life of the device. In order to achieve this algorithms with low computational cost are used (possibly at the expense of some accuracy).

An example of using low computational cost algorithms is the use of difference of area (DOA) methods, which have a low complexity, within waveform analysis. Bin area methods (BAM) may also be used as these provide a trade-off between complexity and accuracy. More generally, it is preferable to use algorithms which analyse time domain features as opposed to those which analyse frequency domain features.

In order to speed up the execution of the Random Forest algorithm, in some embodiments each input feature is discretised so that the volume of information fed to the decision trees is reduced. This approach is used to speed up the execution of the classifier and to reduce the effect of noise by choosing step sizes greater than the fluctuations present in the features on account of noise.

In some embodiments, classifiers are formed using 'distilling'. First, a very complex and computation-intensive neural network is trained. Next, a simpler and faster model is constructed, before being trained it on the output of the former model. This approach results in models (and classifiers) that have the benefits of both speed and accuracy.

'Batching' is another method that is used in some embodiments to speed up computation. If a model has limited processing power and cannot process one heartbeat at a time, the incoming data can be combined into batches of ten heartbeats to reduce the computational burden. This results in the model being up to ten beats behind in making predictions, but enables the use of more accurate models.

In some embodiments, an adversarial training model is used, where cases for which the classifier would misclassify data are determined and these cases are used to improve the performance of the classifiers.

As an example: a neural network is provided that is trained to classify RR sequences. Starting with a healthy rhythm, it is determined which (small) changes need to be made to this rhythm in order for the network to misclassify it as a VT example. This method then enables identification of the weak points of the network. These examples (of misclassified datasets) are subsequently introduced into the training data and the classifiers are trained to classify them correctly. This results in a more robust model with a decreased likelihood of misclassifications.

Figure 8:
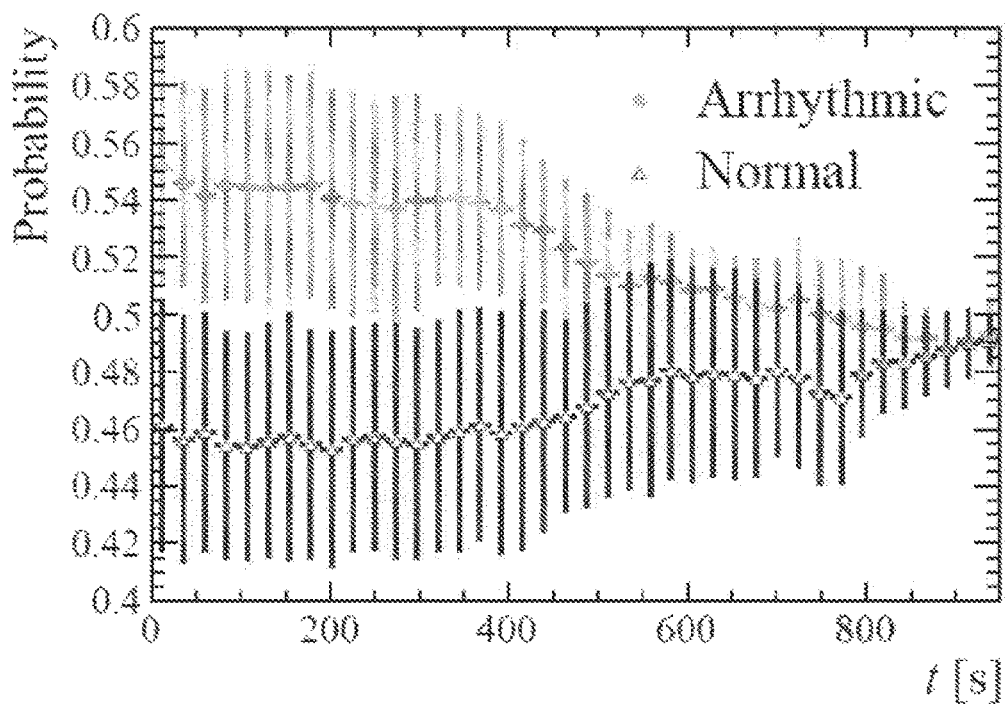
FIG. 8 shows the time evolution of the probability for an arrhythmic episode for the Random Forest classifier.
Figure 9:
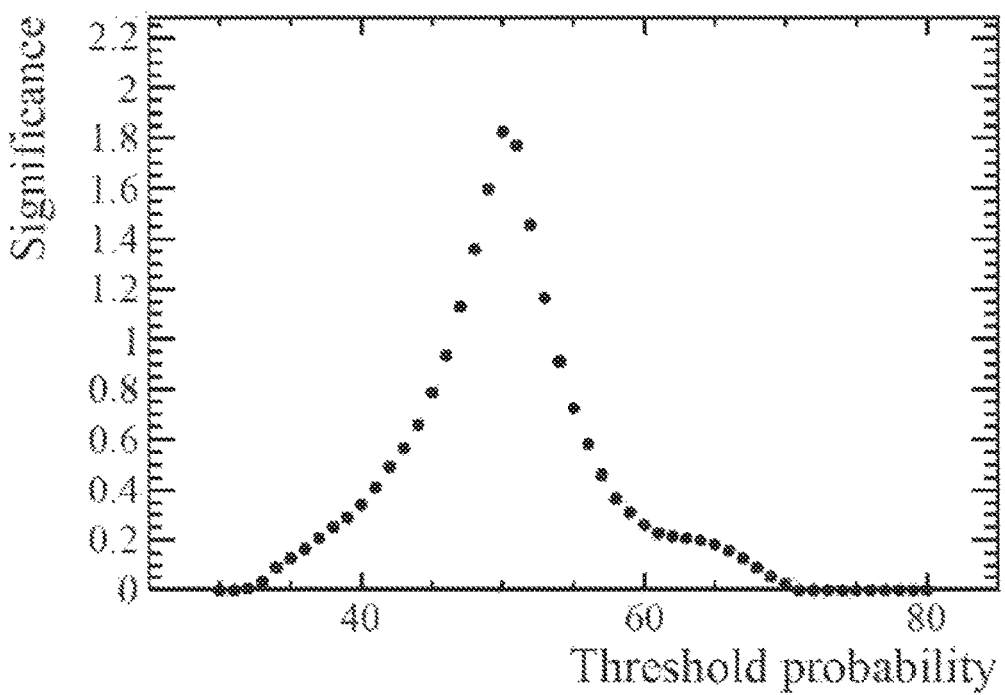
FIG. 9 shows the separation between the 'arrhythmic' and 'normal' probability distributions as a function of probability in units of standard deviations for the Random Forest classifier.

FIG. 8 shows the time evolution of the probability for an arrhythmic episode for the Random Forest classifier. The significance of the separation (between the 'arrhythmic' and 'normal' datasets in standard deviations) as a function of threshold probability is shown for the Random Forest classifier in FIG. 9, which indicates that a threshold of 50% leads to a significance of roughly 1.9 standard deviations.

Figure 10:
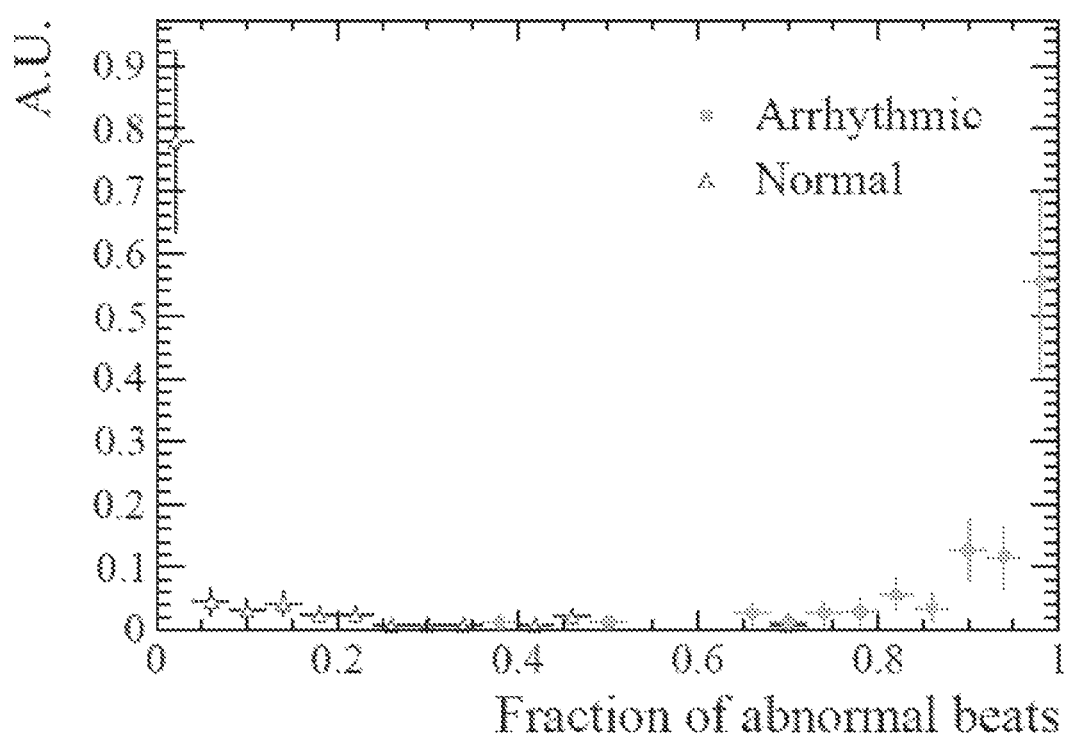
FIG. 10 shows the distribution of fraction of abnormal beats for 'arrhythmic' and 'normal' patients scaled to unit area such that the y-axis scale is in arbitrary units (A.U.)

FIG. 10 illustrates the distributions of abnormality fractions, F—for 'arrhythmic' and 'normal' patients for a Random Forest classifier. The distributions have been normalised to unit area for presentational purposes, where A.U. stands for arbitrary units.

An optimal decision boundary is arrived at by minimising the root mean square error, denoted as RMSE, and defined as:

$$RMSE = \sum_i (F_i - F_{decision})^2 \quad \text{(Equation 1.1)}$$

Where $F_i$ is the fraction of abnormal heartbeats for the ith misclassified patient and $F_{decision}$ is the abnormality fraction under consideration. RMSE can be thought of as a measure of distance from the decision boundary for misclassifications.

A hybrid classifier may be created by combining the abnormality fractions, F, for each model listed above. The combination is a weighted sum defined as:

$$F_{hybrid} = \sum_j (w_j F_j) \quad \text{(Equation 1.2)}$$

Where $w_j$ is the weight attributed to the jth classifier and $F_j$ is the corresponding abnormality fraction, F. The weights, $w_j$, are determined according to the performance of the classifiers, as measured by their RMSE value.

More specifically, the weights, wj, are determined dependent upon their RMSE value over misclassifications. The motivation for doing so is to achieve optimal performance of the resulting hybrid classifier in an unbiased way. Other commonly used metrics could lead to the wrong weights being attributed to classifiers and, consequently, suboptimal decisions.

The performance of the method described herein may be determined according to three metrics, listed below:

Accuracy (A), defined as:

$$A = \frac{TP + TN}{TP + TN + FP + FN} \quad \text{(Equation 1.3)}$$

Where the numerator is a sum of true positives (TP) and true negatives (TN) and the denominator includes false positives (FP) and false negatives (FN).

Sensitivity (SE), defined as:

$$SE = \frac{TP}{TP + FN} \quad \text{(Equation 1.4)}$$

Specificity (SP), defined as:

$$SP = \frac{TN}{TN + FP} \quad \text{(Equation 1.5)}$$

The method described herein may be integrated with and/or implemented by existing patient monitoring equipment.

System Architecture

Figure 11:
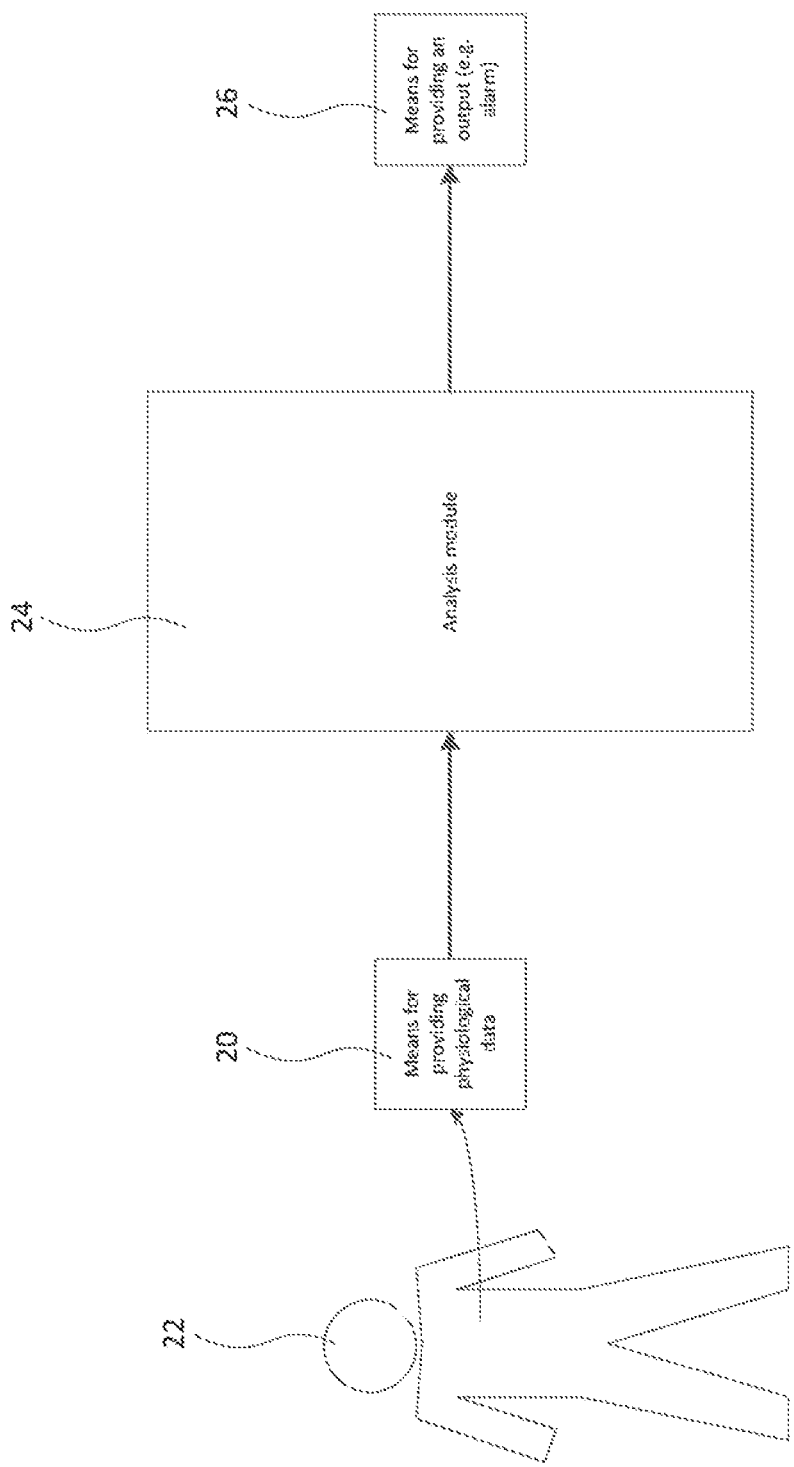
FIG. 11 shows an exemplary system for predicting cardiac events.

FIG. 11 illustrates an example of a system for predicting cardiac events. A physiological data source 20 (e.g. means for providing physiological data), extracted from the cardiorespiratory system of a patient 22, is communicated to an analysis module 24, which analyses the extracted physiological data. This communication may occur over a wired connection or a wireless network. The physiological data source 20 can be, for example, an electrocardiogram (ECG) machine; a pulsometer; a wearable cardioverter defibrillator; an implantable cardioverter defibrillator; a respiratory monitor; and/or a capnography monitor.

The analysis module 24 is configured to evaluate the extracted physiological data, for example evaluating a property of multiple heartbeats in the data, and determine whether said property exceeds an abnormality threshold. This information is then used to derive a probability of the patient experiencing a cardiac event, for example using the method described above in relation to FIGS. 2a and 2b to evaluate said property and derive said property.

The analysis module 24 comprises a hybrid classifier trained and operating as described above in relation to FIG. 2b. The module 24 may comprise part of a dedicated machine, for example running locally to the patient and data source, or be part of a network, running on a server or in the "cloud".

If the analysis module 24 determines that the probability of the patient experiencing a cardiac event in a subsequent time period is above some pre-defined threshold, then the analysis module will trigger a means for providing an output 26, for example an alarm, or other alert, that can alert a healthcare provider that the patient is at risk. This can enable the healthcare provider to take preventative action.

Display of Output

The output displays one or more probabilities, as determined using the methods described. The probabilities are output in numerous forms, notably:

A binary assessment is used as a threshold indicator, where a critical value triggers an alarm. This is particularly useful as a first indicator that a patient may require attention. A threshold here is used to indicate that urgent help is required, or that patient data should be looked at more closely. There may be multiple thresholds which each have a differing level of urgency.

A probability of a cardiac event is output, where this allows a user to allocate resources, and make other decisions, appropriately. An uncertainty estimate is output alongside this probability.

In differing embodiments, the probability is output quantitatively (for example as a percentage risk) and/or qualitatively, (for example a patient may be categorised as one of low risk, medium risk, or high risk, where these correspond to probability ranges). A qualitative measure may be used to simplify the immediate interpretation by a user.

A probability density function is output, where this allows a user to more fully assess a situation.

These probabilities are typically used in conjunction so that, upon a threshold risk being passed, a user is directed to view a probability, or a probability function, to determine an appropriate action. This can then be used as a general indicator of a patient's health, where an increased likelihood of a cardiac event indicates that a patient is more likely to need attention during a certain period.

An uncertainty also being displayed further aids the determination of an appropriate action. A potential problem with any data based analysis, particularly an analysis of a complex situations, such as the prediction of a cardiac event, is that a precise result is rarely achievable; this leads to a figure (such as a probability) on its own having limited use—especially due to the difficulty in determining if this figure is reasonable. The inclusion of an uncertainty based measure (such as a variance, or error bounds), enables a better judgement to be made regarding any given figure/probability.

Advantageously, a probability enables a user to make a rapid assessment, as a probability is intuitively interpreted more easily than, for example, a risk score. Additionally, a probability density function gives a user a large amount of information in a concise format.

In various embodiments, probabilities are also output for a number of timeframes. An initial output is simply a probability without any time reference. A more useful output is a probable time-to-cardiac-event. More specifically, probabilities may be output for time ranges, where this allows efficient allocation of resources.

The outputting of probability density functions for numerous timeframes enables limited resources to be scheduled effectively: for example a limited number of staff to be directed to be ready to assist certain patients at times of increased risk; a probability density function may be used to assess whether a cardiac event is almost certain or whether the risk is more unpredictable.

In some embodiments, a probability density function is displayed numerically, where a mean, a standard deviation, and a kurtosis (indicating the skew of the distribution) are displayed. In these, or other, embodiments, the function is (also) displayed graphically.

There are, in some embodiments, numerous, user selectable, ways to illustrate a probability, for example a best fit normal distribution, a skew normal distribution, or a Poisson distribution. A preferred distribution is suggested during analysis, where a suitable distribution depends on, for example, the amount of information available.

In some embodiments, the probability assessment is continuously updated, where this occurs as relevant information is obtained. An initial assessment uses historic data, and/or admissions data; this initial assessment is then updated (and improved) using recorded and evaluated data (such as the RR intervals above) as it becomes available.

In preferred embodiments, a Bayesian probabilistic framework is used in this updating, where Bayesian inference is used to obtain a probability. This is related to a form of Bayes rule, which is displayed in equation 2.1 below:

$$P(Y|X,\alpha) = \frac{P(X|Y)P(Y|\alpha)}{P(X|\alpha)} \propto P(X|Y)P(Y|\alpha) \quad \text{(Equation 2.1)}$$

where: $P(Y|\alpha)$ is the prior distribution (i.e. the previously calculated probability);

$P(Y|X,\alpha)$ is the posterior distribution (i.e. the updated probability);

$P(X|\alpha)$ is the marginal likelihood (i.e. the likelihood of the recently sampled data given the entire set of data);

$P(X|Y)$ is the sampling distribution (i.e. the probability of the observed data given the current distribution); and $\alpha$ is the hyperparameter of the parameter distribution (i.e. $Y \sim P(Y|\alpha)$).

This equation is used to derive an updated probability based upon a prior probability and the probability of the occurrence of the recently sampled data. Using this equation, recent data which is indicative of a cardiac event being likely would be more concerning in a patient previously judged to be high-risk than it would in a patient previously judged to be low-risk (an interpretation of this is that in the low-risk patient this data is more likely to be anomalous). The use of Bayesian inference is then useful for reducing the rate of false positives, as the prior probability will be small for low-risk patients.

Notably, in the given example, the occurrence of data indicative of a cardiac event would be unlikely given the prior distribution, and so this would have a significant effect on the posterior distribution. Due to this, the data would not simply be written off entirely as anomalous; while it may not immediately result in a warning, continued occurrence of data indicative of a likely cardiac event would rapidly increase the probability (so that the chance of missing a cardiac event is unlikely); however, advantageously, a single (potentially anomalous) datapoint would not trigger a false positive warning.

To further reduce the likelihood of false negatives, in some embodiments, a Bayesian inference model is used alongside a threshold marginal likelihood: a marginal likelihood which is indicative of a very high chance of an upcoming cardiac event then triggers a warning even if the overall probability remains low due to a consistently low prior probability.

The updating of the probability takes place periodically (for example each five seconds, or each minute), where a longer update (or refresh) period use less computing power. This update period is, in some embodiments, small enough that the probability is updated effectively continuously (i.e. the period is so small as to not be noticeable by a user).

In some embodiments, there is a component within the apparatus which allows a choice of the update period—this may also be selectively determined based on the use of the apparatus (where an implanted device may prioritise battery longevity over rapid updates).

A consideration here is that, in many situations, it is possible to maintain an accurate probability while making only periodic updates, especially where there is a large prior distribution (i.e. where measurements have been taken for a long time). The update period is then based upon the prior distribution. As an upper limit for the time, these updates may be limited, so as to be regular enough that they do not miss a cardiac event.

Figure 12:
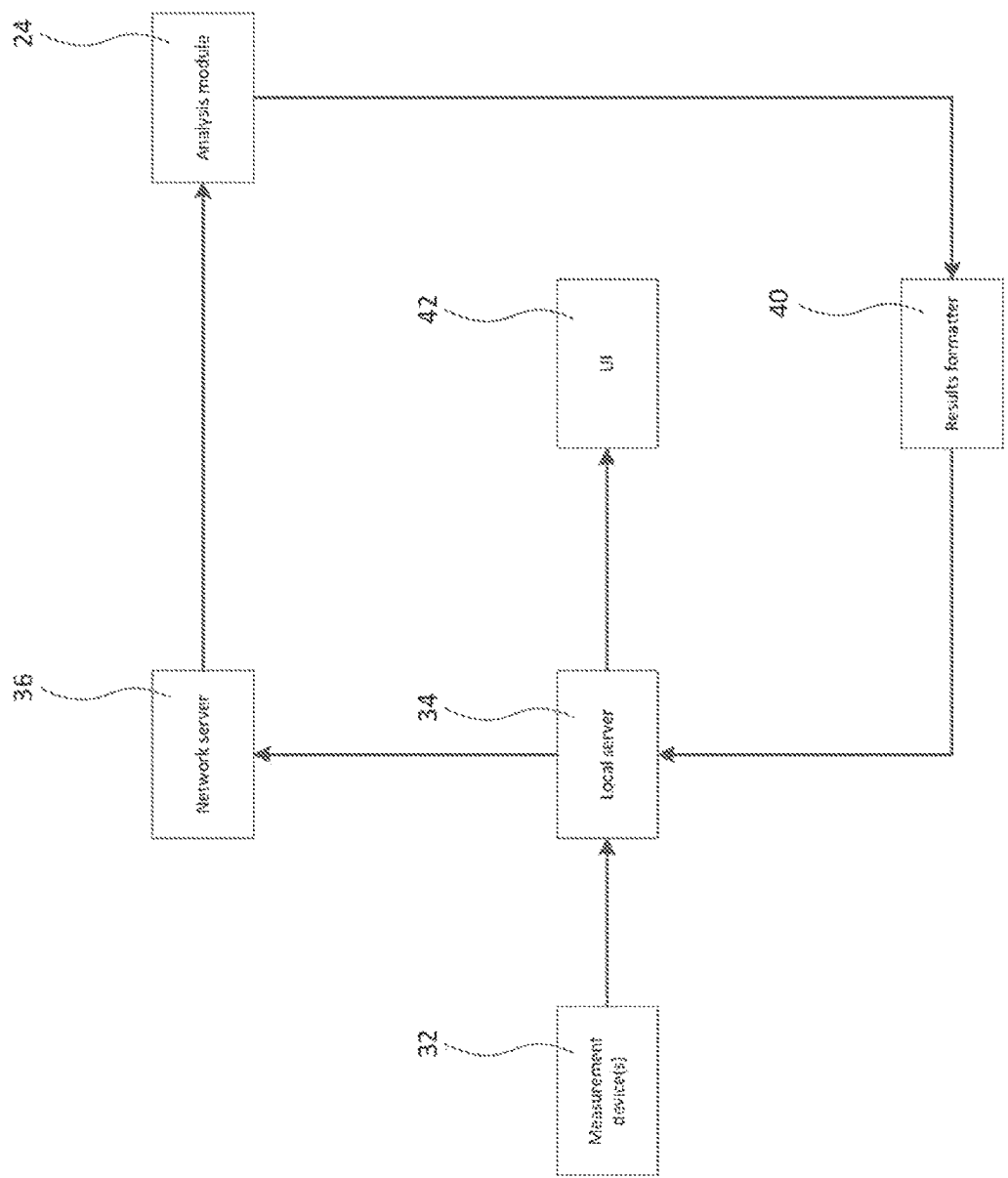
FIG. 12 shows a component diagram for analysing patient data and displaying an output.

FIG. 12 shows a component diagram for analysing patient data and displaying an output.

One or more measurement device(s) (e.g. an ECG, a patient file) 32 transmit(s) data to a local server 34. These data are then transmitted to a network server 36, and fed through an analysis module 24 (as discussed above, e.g. with reference to FIG. 2b). The output of the classifier passes through a results formatter 40 before being transmitted back to the local server 34 (this results formatter 40, for example, format results to be output as a warning alarm, or a display of probability). The output is then be presented on a UI 42 for one or more users, this uses, for example, a smartphone, a screen, or a display distributed by a hospital. In some embodiments, this also comprises a speaker, which provides an audible output if a threshold probability is exceeded.

By sending data via a network server 36, instead of storing all data on a local device, the data can be displayed to numerous users simultaneously. This allows the gathering multiple opinions, or to alert numerous users simultaneously, so that the user in the best position to may be notified.

The use of a network server 36 also enables remote monitoring of a patient. This may be used for a patient with an implantable device, where data recorded by the device is transferred to a network server 36, evaluated by the analysis module 24, and then displayed on a UI 42 to both the user and (separately) a healthcare professional, who may then check on the user at an appropriate time.

The figures as described above show a system for monitoring a patient. As a general overview: in FIG. 11, there is a patient 22, for which it is desired to output a probability of a cardiac event. A means for providing physiological data 20, such as an electrocardiogram (ECG) is used to obtain this data. Typical data is shown in FIG. 1; specific data, such as the RR intervals is extracted from this data. This data is then fed into an analysis module 24, which is discussed with reference to FIG. 2b.

Figure 2B:
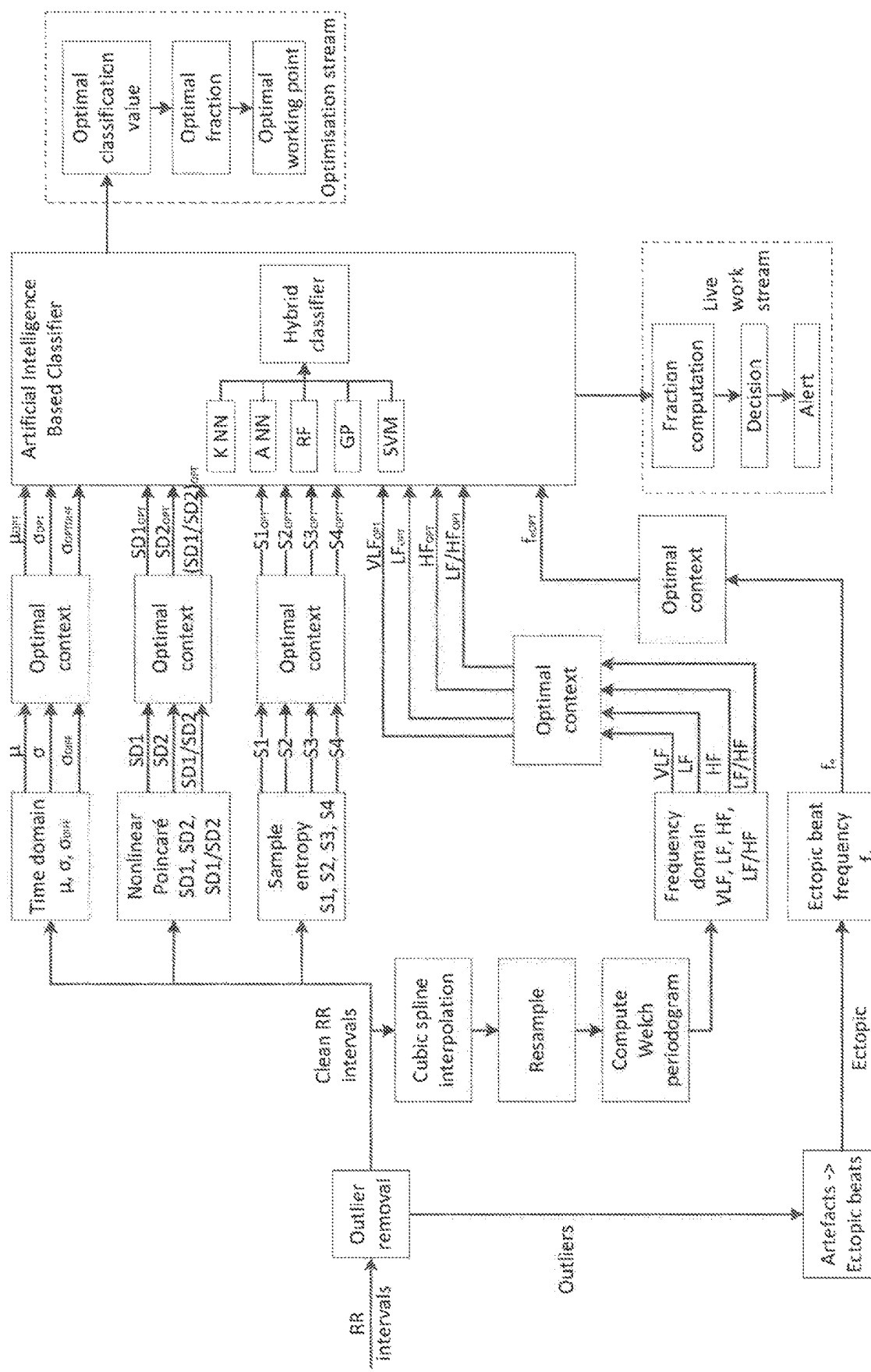
FIG. 2b is a specific process flowchart for the method described herein as pertaining to one of the possible inputs to the algorithm.

The analysis module 24 is provided with the specific data (the RR intervals) as in FIG. 2b. Processing then occurs:
1. outliers are removed. This is demonstrated by FIG. 3;
2. numerous properties are determined, such as the mean RR interval, and the ectopic beat frequency;
3. optimal context lengths are determined for each property (or for a grouping of properties, such as time domain properties). This is demonstrated by FIG. 7;
4. the optimal length of data is fed into an artificial intelligence based classifier;
5. the artificial intelligence based classifier, which is formed of multiple different classifiers combined to obtain a hybrid classifier, determines threshold abnormality values for each property, which are indicative of an upcoming cardiac event (e.g. a threshold mean RR interval is calculated, where a mean interval above this threshold is indicative of an upcoming cardiac event). The threshold values are determined based upon past data from multiple sources, for example a database containing physiological data for patients alongside occurrences of cardiac events may be used for training a classifier.
6A. The data which has been fed in to the classifier is compared to the relevant threshold, and a probability of a cardiac event occurring is determined (based on the fraction of the data which exceeds the threshold). This probability is displayed, and an alarm is sounded if a high probability of a cardiac event is obtained.
6B. The data which has been fed in to the classifier is output to an optimisation stream, where it is used to further optimise the determination of following threshold values (i.e. it is incorporated into the training set).

This output is then presented using a means for providing an output 26.

The means for providing physiological data, and the means for providing an output are described in more detail above with reference to FIG. 12.

Alternatives and Modifications

Data Types

The use of RR intervals is an example of a type of data—more specifically a type of physiological data, and even more specifically a type of cardiac data—which is usable with the described methods; more generally, any type of patient data, or any combination of types of data could be used with these methods, where the use of a combination of patient data may lead to fewer false positives (or false negatives). Examples of preferred types of data are (with some overlap as, for example, telemetry records and clinical data both comprise physiological data):
- telemetry records, such as arterial blood pressure, pulse contour data, or pulse rate;
- demographic data, such as age, sex, or race (this may come from an electronic health report/patient profile);
- Admission/historic data, such as a recent illness or any history of illness; in particular concomitant conditions, such as emphysema or diabetes;
- clinical data, such as haemoglobin values;
- laboratory data, such as the results of tests;
- imaging data, such as x-rays or MRI scans.

Where multiple data types are considered, each of these types of data is treated similarly to the RR intervals: properties (such as a mean or a standard deviation) are extracted, and an optimal context length for these features determined—as an example, there is an optimal length of patient history to consider, where data more than, for example, 10 years old may have a negligible contribution to a prediction of future health. Numerous data types are considered in the determination of a probability, where, in some embodiments, each data type has a different weighting (where this weighting is based upon historic data and determined by the classifiers).

In various embodiments, the data types used are optimised, where this is used within the display of a probability. In each situation, there is selected a combination of data features with the most significant effect; this is particularly useful where an implantable device is used, and using a low number of data types is desirable, as this minuses the computational burden.

In some embodiments, to avoid the need for new measuring equipment, analysis occurs only using data which is attainable using current measuring methods.

While the data recording methods discussed have primarily involved specialist equipment (e.g. electrocardiograms), the methods discussed could equally be used with other, more widely available equipment. As an example, there exist many user wearable devices which are used to monitor a heartrate or a pulse (such as a Fitbit™) The data recorded using this, or a similar, device could be used with the AI classifier described above to obtain a probability of a cardiac event, or to output a general health measure. If used in such a device, the output may be a displayed probability, or measure of health, to the user, or an automatic warning sent to, for example, an ambulance, if a threshold probability is exceeded. This may be particularly useful in devices such as a Fitbit™, which are used during periods of increased activity (where stress may be placed upon the heart).

Context Length Determination

The context length determination has been explained using the example of a $X^2$-test ('chi-squared' test); numerous other tests could be used to make this determination. Various embodiments use one of (or a combination of): a Kolmogorov-Smirnov test, a comparison of the moments of distributions, or an Energy Test (as described by Guenter Zech and Berkan Asian).

When using the Energy Test an Energy Test metric, T, is computed between two distinct unbinned multivariate distributions. One such example is arrhythmic and normal heartbeat distributions, which give a non-zero T-value. This is used in some embodiments as an additional test on the probability of a cardiac event: an Energy Test is performed and a T-value calculated, this T-value is updated after each heartbeat and a warning is issued if the T-value exceeds a predetermined threshold (which is based on past data, and may be determined for each patient based upon their specific data). The context length over which the Energy Test is performed is determined as with any other dataset. This test may be used in isolation, or in conjunction with any other method described, where use in conjunction with other methods may reduce the likelihood of false negatives or false positives.

Autoregressive Models

In some embodiments, autocorrelation is considered along with a measure of the lag required to obtain an autocorrelation. As an example, in the short term, the occurrence one cardiac event may be indicative of another cardiac event being likely to occur (i.e. recent cardiac events may have high autocorrelation), as these events are often related to periods of otherwise poor health. In the long term, a previously occurring cardiac event (e.g. a cardiac event which occurred in a previous year), may be a poor indicator of a subsequent cardiac event (i.e. distant cardiac events may have low autocorrelation), as the period of poor health may have passed. The suitability of using an autoregressive model is determined by comparing these correlations and lags.

A consideration with autocorrelation is that (useful) autocorrelation may be negative or positive. In the previously used example, it may be the case that a previous, but distant cardiac event (e.g. one that occurred in a previous year), is a good indicator that a cardiac event is unlikely, as the person may have worked to improve their health in response to the previous event.

Other Conditions

The methods described could be used for a range of other conditions, for example, as well as a cardiac event, indicators of an upcoming arrhythmia may also be used to predict a stroke. The methods disclosed herein could also be used to measure conditions away from the heart: the flow of blood could, for example, be monitored as relates to transfer to the brain. In this situation, a context length would still be of relevance: monitoring the blood flow into the brain could be used to give a prediction of brain related events (such as brain aneurysms).

More generally, the methods disclosed could be used as a general indication of health. Abnormal operation of any pulse based condition is a possible indicator of not only the probability of a specific event (e.g. arrhythmia), but also that the patient is likely to be at heightened risk of a more general health-related incident. These methods may then be used to indicate that a patient may need more careful monitoring during a determined period, or that it may be valuable to analyse patient data in more detail and/or to carry out tests.

It will be understood that the invention has been described above purely by way of example, and modifications of detail can be made within the scope of the invention.

Each feature disclosed in the description, and (where appropriate) the claims and drawings may be provided independently or in any appropriate combination.

Reference numerals appearing in the claims are by way of illustration only and shall have no limiting effect on the scope of the claims.

What is claimed is:

1. A method of analysing cardiac data relating to a patient, comprising:
   providing cardiac data relating to the patient;
   identifying a plurality of types of property;
   determining a plurality of context lengths, wherein a context length is determined for each type of property, and wherein each context length defines a number of heartbeats to be used for determining a property;
   determining a plurality of properties of the cardiac data, wherein each property is determined over the determined context length for the type of said property;
   comparing the plurality of properties against one or more predetermined threshold values, thereby to indicate a probability of the patient experiencing a cardiac event; and
   providing an output based on the comparison.

2. The method of claim 1, wherein the threshold value is determined based on a dataset comprising a plurality of data obtained from multiple sources.

3. The method of claim 1, wherein the context length is between 10 and 100,000 heartbeats.

4. The method of claim 1, wherein the context length is an optimally discriminating context length for a combination of types of property.

5. The method of claim 1, wherein the property is determined over a context length which is an optimally discriminating context length for the identified type of property.

6. The method of claim 4, wherein an optimally discriminating context length is determined using at least one of: a chi-squared ($\chi^2$) test, a Kolmogorov-Smirnov test, and an Energy test.

7. The method of claim 1, further comprising:
   providing further data relating to the patient, wherein the further data comprises at least one of: physiological data, demographic data, admission data, past medical history, laboratory data, imaging data;
   determining one or more properties of the further data, wherein the or each property of the further data is determined over a particular context length, the context length being selected based on the property;
   comparing the or each property of the further data against a respective predetermined threshold value for the further data, thereby to indicate a probability of the patient experiencing a cardiac event; and
   providing an output based on the comparison.

8. The method of claim 7, further comprising providing an output based upon a combination of the comparison of the property data and the comparison of the further data.

9. The method of claim 1, wherein the data comprises data from multiple heartbeats and/or wherein the data comprises RR intervals of multiple heartbeats, for example as indicated on an electrocardiogram (ECG).

10. The method of claim 9, further comprising at least one of: processing the data in batches, processing the data in batches of a size of at least 5 heartbeats.

11. The method of claim 1, wherein the type of property comprises at least one of: a property of multiple heartbeats; a mean of multiple heartbeats; a standard deviation of multiple heartbeats; a standard deviation in successive differences of multiple heartbeats; a measured heart rate variability (HRV) of a patient; and a fraction of multiple heartbeats that exceed an abnormality threshold.

12. The method of claim 1, further comprising calculating a rate of change of the property.

13. The method of claim 1, wherein the property is compared against the respective predetermined value for a given time window.

14. The method of claim 1, wherein the output comprises triggering an alert when the indicated probability exceeds a predetermined probability threshold and/or wherein the indicated probability comprises an indication of a corresponding time and/or a display of a period of highest risk.

15. The method of claim 1, wherein the indicated probability is determined using Bayesian inference.

16. The method of claim 1, wherein the indicated probability comprises an indication of a corresponding time and/or a display of a period of highest risk.

17. The method of claim 1, wherein the respective predetermined threshold is determined by:
training at least two classifiers to classify a property of multiple heartbeats within the cardiac data using at least one machine learning algorithm; and
combining the at least two classifiers to produce a hybrid classifier;
wherein the combination is based on a performance metric.

18. A system for analysing cardiac data relating to a patient, comprising:
a data module for providing cardiac data relating to the patient;
an analysis module for:
identifying a plurality of types of property;
determining a plurality of context lengths, wherein a context length is determined for each type of property, and wherein each context length defines a number of heartbeats to be used for determining a property;
determining a plurality of properties of the cardiac data, wherein each property is determined over the determined context length for the type of said property;
a comparison module for comparing the plurality of properties against one or more predetermined threshold values, thereby to indicate a probability of the patient experiencing a cardiac event; and
a presentation module for providing an output based on the comparison.

19. The system of claim 18, wherein the data module comprises at least one of: an electrocardiogram (ECG) machine; a pulsometer; a wearable cardioverter defibrillator; an implantable cardioverter defibrillator; a respiratory monitor; and a capnography monitor, or other such source extracting data from the cardiorespiratory system of a patient.

20. An apparatus for analysing patient health using data relating to a patient, comprising:
an analysis module for:
identifying a plurality of types of property;
determining a plurality of context lengths, wherein a context length is determined for each type of property, and wherein each context length defines a number of heartbeats to be used for determining a property;
determining a plurality of properties of the cardiac data, wherein each property is determined over the determined context length for the type of said property;
a comparison module for comparing the properties against one or more predetermined threshold values, thereby to indicate a probability of the patient experiencing a cardiac event; and
a presentation module for providing an output based on the comparison.

* * * * *

UNITED STATES PATENT AND TRADEMARK OFFICE
CERTIFICATE OF CORRECTION

PATENT NO. : 11,497,430 B2
APPLICATION NO. : 16/491164
DATED : November 15, 2022
INVENTOR(S) : Marek Sirendi et al.

It is certified that error appears in the above-identified patent and that said Letters Patent is hereby corrected as shown below:

On the Title Page

Item (30) Foreign Application Priority Data:
"1703662" should be changed to --1703662.5--

Signed and Sealed this
Twenty-eighth Day of February, 2023

Katherine Kelly Vidal
*Director of the United States Patent and Trademark Office*